United States Patent
Nomura et al.

(10) Patent No.: US 7,718,571 B2
(45) Date of Patent: *May 18, 2010

(54) METHOD OF CULTIVATING FRUIT VEGETABLES IN AN INCREASED YIELD

(75) Inventors: Takayuki Nomura, Wakayama (JP); Masatoshi Kamei, Wakayama (JP); Toshio Hayashi, Wakayama (JP)

(73) Assignee: Kao Corporation, Tokyo (JP)

( * ) Notice: Subject to any disclaimer, the term of this patent is extended or adjusted under 35 U.S.C. 154(b) by 450 days.

This patent is subject to a terminal disclaimer.

(21) Appl. No.: 11/179,618

(22) Filed: Jul. 13, 2005

(65) Prior Publication Data

US 2006/0014646 A1    Jan. 19, 2006

(30) Foreign Application Priority Data

Jul. 14, 2004    (JP) .............................. 2004-207471

(51) Int. Cl.
    *A01N 25/00*    (2006.01)
(52) U.S. Cl. ................................... 504/116.1
(58) Field of Classification Search ............... 504/116.1
    See application file for complete search history.

(56) References Cited

U.S. PATENT DOCUMENTS

| | | | |
|---|---|---|---|
| 4,150,970 A | 4/1979 | Ries et al. | |
| 4,167,641 A | 9/1979 | Welebir | |
| 2003/0216261 A1* | 11/2003 | Hayashi et al. | ............. 504/353 |
| 2004/0142822 A1 | 7/2004 | Suzuki et al. | |

FOREIGN PATENT DOCUMENTS

| | | | |
|---|---|---|---|
| EP | 1114584 | * | 5/1999 |
| EP | 0 998 850 | A1 | 5/2000 |
| EP | 1 114 584 | A1 | 7/2001 |
| EP | 1 366 663 | A1 | 12/2003 |
| JP | 55-40674 | A | 3/1980 |
| JP | 9-322647 | A | 12/1997 |
| JP | 2000-198703 | | 7/2000 |
| JP | 2002-265305 | A | 9/2002 |
| WO | WO-02/071842 | A1 | 9/2002 |
| WO | WO-02/074081 | A1 | 9/2002 |

* cited by examiner

*Primary Examiner*—Johann R Richter
*Assistant Examiner*—Kristie L Brooks
(74) *Attorney, Agent, or Firm*—Birch, Stewart, Kolasch & Birch, LLP.

(57) ABSTRACT

The invention provides a method wherein a treating solution containing a compound (A) of specific structure having a C10 to C22 hydrocarbon group at a concentration of 1 to 1000 ppm is applied at least once in a period of from germination of a fruit vegetable to planting in a field and applied at least once after planting in the field.

5 Claims, No Drawings

METHOD OF CULTIVATING FRUIT VEGETABLES IN AN INCREASED YIELD

FIELD OF THE INVENTION

The present invention relates to a method of cultivating fruit vegetables such as a tomato, a cucumber, a strawberry, a green pepper and an eggplant in an increased yield.

BACKGROUND OF THE INVENTION

An attempt to increase the yield by promoting the growth of crops and increasing the yield per unit area is a task important in agricultural production. Usually, major three elements essential for plant growth, that is, nitrogen, phosphorus and potassium, and nutrient elements such as trace metal elements, are incorporated into a fertilizer and an additional fertilizer and supplied to plants, but the amount and yield of grown crops are generally limited even if the concentration of the nutrient elements in the fertilizer is increased, and by using the fertilizer in a larger amount, the nutrient elements come to be in excess in the soil thus worsening the balance of absorption and causing a reduction in plant growth, resulting in problems such as failure to achieve the intended increase in yield and failure to improve qualities such as sugar degree (Brix value) and freshness (greenness). Under these circumstances, combined use of various plant growth regulators has been carried out.

As the plant growth regulator, plant growth regulators represented by gibberellin and auxin are used in regulation of growth and morphogenetic reaction such as germination, rooting, elongation, flowering and fruit setting. Further, there are known techniques wherein a leaf spray using an oligosaccharide (JP-A 9-322647) or a liquid fertilizer containing sugars, minerals, amino acids, a seaweed extract or a microbial fermentation extract is sprayed onto leaves or applied in the form of a solution. JP-A 55-40674 discloses use of a C30 alcohol as a plant growth promoter. JP-A 2000-198703 discloses a plant activating agent containing a C12 to C24 monovalent alcohol. JP-A 2002-265305 discloses an agent for increasing the yield of crops, which contains a specific compound such as a C12 to 24 monovalent alcohol.

SUMMARY OF THE INVENTION

The present invention relates to a method of cultivating a fruit vegetable in an increased yield, which includes applying a treating solution containing a compound (A) represented by the following general formula (1) at a concentration of 1 to 1000 ppm at least once in a period of from germination of a fruit vegetable to planting in a field (hereinafter, referred to as application onto seedlings) and then applying it at least once after planting in the field (hereinafter, referred to as application onto the field).

The term "increased yield" means an increase in the amount of an intended site of harvested fruit vegetables.

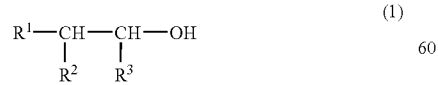

wherein $R^1$ represents a C10 to C22 hydrocarbon group, $R^2$ represents a hydrogen atom, a hydroxyl group or a C1 to C24 hydrocarbon group, and $R^3$ represents a hydrogen atom or a C1 to C24 hydrocarbon group.

DETAILED DESCRIPTION OF THE INVENTION

Conventionally, there is a need for further improving an effect of increasing the final yield of crops. JP-A 2002-265305 supra refers to conditions regarded effective for increasing the yield of crops, but not to conditions that are optimum depending on the type of crops. In particular, the optimum conditions for fruit vegetables such as a tomato, a cucumber, a strawberry, a green pepper and an eggplant are not referred to.

The present invention provides a cultivating method more excellent in the effect of increasing the yield of crops, particularly fruit vegetables.

According to the present invention, there is provided a method of cultivating fruit vegetables in an increased yield wherein a significant effect of increasing the yield is stably achieved.

<Compound (A)>

In the general formula (1), the hydrocarbon groups represented by $R^1$, $R^2$ and $R^3$ may be respectively saturated or unsaturated groups, preferably saturated groups, and may be linear, branched or cyclic chains, preferably linear or branched chains, particularly preferably linear chains. The number of total carbons in the hydrocarbon group may be either an odd number or an even number, preferably an even number.

The number of total carbons in $R^1$, $R^2$ or $R^3$ is preferably 50 or less, more preferably 12 to 48, still more preferably 16 to 44.

In the general formula (1), the number of carbons in $R^1$ is preferably 14 to 22, more preferably 14 to 20, still more preferably 14 to 18. The number of total carbons in the compound represented by the general formula (1) is preferably 12 to 48, more preferably 16 to 28, still more preferably 16 to 24. The compound is more preferably a compound containing 12 to 24 carbons in total and having one hydroxyl group, still more preferably a compound containing 16 to 22 carbons in total and having one hydroxyl group. Examples of the compound represented by the general formula (1) include the followings:

(A1) 1-Alkanol represented by $CH_3(CH_2)_{o-1}OH$ wherein o is an integer of 12 to 24, preferably 16 to 24, more preferably 16 to 20, is mentioned. That is, the C12 to C24 monovalent alcohol is mentioned as the compound represented by the general formula (1). Specific examples include 1-dodecanol, 1-tridecanol, 1-tetradecanol, 1-pentadecanol, 1-hexadecanol, 1-heptadecanol, 1-octadecanol, 1-nonadecanol, 1-icosanol, 1-heneicosanol, 1-docosanol, 1-tricosanol, 1-tetracosanol etc.

(A2) 2-Alkanol represented by $CH_3CH(OH)(CH_2)_{p-3}CH_3$ wherein p is an integer of 12 to 24, preferably 16 to 24, more preferably 16 to 20, is mentioned. Specific examples include 2-dodecanol, 2-tridecanol, 2-tetradecanol, 2-pentadecanol, 2-hexadecanol, 2-heptadecanol, 2-octadecanol, 2-nonadecanol, 2-icosanol etc.

(A3) An alcohol unsaturated in the end, represented by $CH_2=CH(CH_2)_{q-2}OH$ wherein q is an integer of 12 to 24, preferably 16 to 24, more preferably 16 to 20, is mentioned. Specific examples include 11-dodecen-1-ol, 12-tridecen-1-ol, 15-hexadecen-1-ol etc.

(A4) Other unsaturated long-chain alcohols include oleyl alcohol, elaidyl alcohol, linoleyl alcohol, linolenyl alcohol, eleostearyl alcohol (α or β), ricinoyl alcohol etc.

(A5) 1,2-Diol represented by $HOCH_2CH(OH)(CH_2)_{r-2}H$ wherein r is an integer of 12 to 24, preferably 16 to 24, more preferably 16 to 20, is mentioned. Specific examples include 1,2-dodecanediol, 1,2-tetradecanediol, 1,2-hexadecanediol, 1,2-octadecanediol etc.

Among the above-mentioned (A1) to (A5), (A1), (A2), (A4) and (A5) are preferable, (A1), (A2) and (A4) are more preferable, (A1) and (A4) are still more preferable, and (A1) is still more preferable.

<Treating Solution>

The treating solution used in the present invention contains the compound (A) at a concentration of 1 to 1000 ppm (ratio by weight; this hereinafter applies), preferably 1 to 500 ppm, more preferably 1 to 300 ppm.

Preferably, the treating solution used in the present invention contains at least one member selected from a surfactant (B) [referred to hereinafter as component (B)] other than the compound (A), a chelating agent (C) [referred to hereinafter as component (C)] and a fertilizer (D) [referred to hereinafter as component (D)], together with the compound (A). Particularly, the components (B) and (C) are preferably simultaneously used. When the fertilizer is necessary at the time of application, for example the compounds (B), (C) and (D) are preferably used in combination with the compound (A). When the fertilizer is not necessary at the time of application, for example the components (B) and (C) are preferably used in combination with the compound (A).

<Component (B)>

As component (B), the following surfactant is used preferably for the purpose of emulsifying, dispersing or solubilizing the compound (A), or promoting the permeation thereof.

The nonionic surfactants include sorbitan fatty ester, polyoxyalkylene sorbitan fatty ester, polyoxyalkylene fatty ester, glycerin fatty ester, polyoxyalkylene glycerin fatty ester, polyglycerin fatty ester, polyoxyalkylene polyglycerin fatty ester, sorbitol fatty ester, polyoxyalkylene sorbitol fatty ester, sucrose fatty ester, resin acid ester, polyoxyalkylene resin acid ester, polyoxyalkylene alkyl ether, polyoxyalkylene alkyl phenyl ether, alkyl(poly)glycoside, polyoxyalkylene alkyl(poly)glycoside, alkyl alkanol amide, sugar-based fatty acid amide, etc. The sugar-based fatty acid amide includes, for example, those having a structure containing a hydrophobic group bound via an amide linkage to glucose or sugar alcohol, for example sugar-based fatty amides such as glucose or fructose fatty acid amides. Use can also be made of those having a structure containing a hydrophobic group bound via an amide linkage to amino-containing sugar or sugar alcohol, for example sugar-based fatty acid amides such as N-methyl glucamine fatty acid amides. The nonionic surfactant is preferably at least one member selected from a nitrogen atom-free, ether group-containing nonionic surfactant and an ester group-containing nonionic surfactant. Preferable examples include polyoxyalkylene (particularly ethylene) sorbitan fatty ester, polyoxyalkylene (particularly ethylene) glycerin fatty ester, and sucrose fatty ester.

The surfactant includes anionic surfactants such as carboxylic acid-, sulfonic acid-, sulfate- and phosphate-based surfactants, and is preferably at least one member selected from carboxylic acid- and phosphate-based surfactants.

The carboxylic acid-based surfactant includes, for example, C6 to C30 fatty acid or salts thereof, polyvalent carboxylates, polyoxyalkylene alkyl ether carboxylates, polyoxyalkylene alkyl amide ether carboxylates, rosinates, dimer acid salts, polymer acid salts, tall oil acid fatty acid salts, esterified modified starch etc. Among these surfactants, esterified modified starch is preferable. Among these esterified modified starch, an alkenyl succinic acid-modified starch, alternatively called an alkenyl succinic acid-esterified starch or an alkenyl succinic acid starch, is preferable. Octenyl succinic acid starch is more preferable, for example Emulstar #30, produced by Matsutani Chem.Ind.Co.Ltd., as a commercial product.

The sulfonic acid-based surfactant includes, for example, alkyl benzene sulfonates, alkyl sulfonates, alkyl naphthalene sulfonates, naphthalene sulfonates, diphenyl ether sulfonates, alkyl naphthalene sulfonate condensates, naphthalene sulfonate condensates, etc.

The sulfate-based surfactant includes, for example, alkyl sulfates, polyoxyalkylene alkyl sulfates, polyoxyalkylene alkyl phenyl ether sulfates, tristyrene phenol sulfates, polyoxyalkylene distyrene phenol sulfates, alkyl polyglycoside sulfates etc.

The phosphate-based surfactant includes, for example, alkyl phosphates, alkyl phenyl phosphates, polyoxyalkylene alkyl phosphates, polyoxyalkylene alkyl phenyl phosphates etc.

The salt includes, for example, metal salts (Na, K, Ca, Mg, Zn etc.), ammonium salts, alkanol amine salts, fatty amine salts etc.

The amphoteric surfactants include amino acid-, betaine-, imidazoline- and amine oxide-based surfactants.

The amino acid-based surfactant includes, for example, acyl amino acid salts, acyl sarcosinate, acryloyl methyl amino propionate, alkyl amino propionate, acyl amide ethyl hydroxy ethyl methyl carboxylate, etc.

The betaine-based surfactant includes alkyl dimethyl betaine, alkyl hydroxy ethyl betaine, acylamide propyl hydroxy propyl ammonia sulfobetaine, ricinoleic acid amide propyl dimethyl carboxy methyl ammonia betaine, etc.

The imidazole-based surfactant includes alkyl carboxy methyl hydroxy ethyl imidazolium betaine, alkyl ethoxy carboxy methyl imidazolium betaine, etc.

The amine oxide-based surfactant includes alkyl dimethyl amine oxide, alkyl diethanol amine oxide, alkyl amide propyl amine oxide etc.

The component (B) may be one kind of component or a mixture of two or more thereof. When the component (B) contains polyoxyalkylene groups, the component is the one preferably having polyoxyethylene groups, wherein the number of these groups added on average is 1 to 300, preferably more than 5 to not more than 100.

The component (B) is the one wherein the Griffin's HLB is preferably 10 or more, more preferably 12 or more.

When a C12 to C24 monovalent alcohol is used as the component (A), the component (B) is preferably at least one member selected from an ester group-containing nonionic surfactant, a nitrogen atom-free, ether group-containing nonionic surfactant, an amphoteric surfactant, a carboxylic acid-based anionic surfactant and a phosphate-based anionic surfactant. The component (B) is particularly preferably at least one member selected from an ester group-containing nonionic surfactant and a nitrogen atom-free, ether group-containing nonionic surfactant. That is, the treating solution used in the present invention includes a solution containing a C12 to C24 monovalent alcohol and at least one kind of surfactant selected from an ester group-containing nonionic surfactant, a nitrogen atom-free, ether group-containing nonionic surfactant, an amphoteric surfactant, a carboxylic acid-based anionic surfactant and a phosphate-based anionic surfactant.

<Component (C)>

The following organic acid (or a salt thereof) having a chelating ability can be simultaneously used to further improve the effect of increasing the yield of crops. Specific examples include oxycarboxylic acids and polyvalent carboxylic acids such as citric acid, gluconic acid, malic acid, heptonoic acid, oxalic acid, malonic acid, lactic acid, tartaric acid, succinic acid, fumaric acid, maleic acid, adipic acid, glutaric acid etc., as well as salts thereof such as potassium salts, sodium salts, alkanolamine salts, fatty amine salts, etc. A chelating agent other than the organic acid can also be mixed to improve the yield of crops. The chelating agent mixed includes aminocarboxylic acid-based chelating agents such as EDTA, NTA, CDTA etc.

<Component (D)>

Specific examples of the component (D) include inorganic and organic materials serving as a source for supplying N, P, K, Ca, Mg, S, B, Fe, Mn, Cu, Zn, Mo, Cl, Si, Na etc., particularly N, P, K, Ca and Mg. Such inorganic materials include ammonium nitrate, potassium nitrate, ammonium sulfate, ammonium chloride, ammonium phosphate, soda nitrate, urea, ammonium carbonate, potassium phosphate, lime perphosphate, fused phosphate fertilizer ($3MgO \cdot CaO \cdot P_2O_5 \cdot 3CaSiO_2$), potassium sulfate, potassium chloride, lime nitrate, slaked lime, lime carbonate, magnesium sulfate, magnesium hydroxide, magnesium carbonate etc. The organic materials include fowl droppings, cow dung, bark manure, amino acid, peptone, Mieki (amino acid solution), fermentation extract, calcium salts of organic acids (citric acid, gluconic acid, succinic acid etc.), calcium salts of fatty acids (formic acid, acetic acid, propionic acid, caprylic acid, capric acid, caproic acid etc.), etc. These fertilizer components can also be used in combination with the surfactant. Incorporation of the fertilizer components is not always necessary where the fertilizer components have previously been applied sufficiently to the soil, such as in outdoor raising of a rice plant or vegetables. Incorporation of the fertilizer components is preferable for culture forms such as a fertigation (a hydroponic soil culture) or a hydroponics where the fertilizer components are given by irrigation while excessive application of the fertilizer is avoided.

When the components (B) to (D) are simultaneously used in the treating solution used in the present invention, the ratio of each component to 100 parts by weight of the compound (A) is as follows: The component (B) is preferably 10 to 20,000 parts by weight, more preferably 100 to 2,000 parts by weight; the component (C) is preferably 0 to 50,000 parts by weight, more preferably 10 to 5,000 parts by weight; and the component (D) is preferably 0 to 1,000,000 parts by weight, more preferably 0 to 100,000 parts by weight, still more preferably 10 to 100,000 parts by weight.

In the treating solution used in the present invention, other nutrient sources (sugars, amino acids, vitamins etc.) can be contained in an amount of 0 to 5000 parts by weight, particularly 10 to 500 parts by weight, based on 100 parts by weight of the compound (A).

As the method of supplying the treating solution used in the present invention to fruit vegetables, various means can be used. Examples include a method of spraying the treating solution directly onto plant leaves, stems, fruits etc.(such as leave-spraying) or injecting it into the soil (such as injecting or irrigating) and a method of feeding the treating solution after diluting and mixing it with a hydroponic solution or supplied water contacting with roots in hydroponics or rock wool(such as nutrient solution culture).

The nutrient solution culture includes hydroponic, spraying culture and culture in solid medium. The hydroponics is classified into water-filling culture with circulation, water-filling culture with ventilation, water-filling culture with changed levels, capillary-culture and NFT (nutrient film technique). Spraying-culture is classified into sprayed hydroponic culture and spraying medium culture etc. Culture in solid medium is classified into culture in inorganic medium and culture in organic medium. In the culture in inorganic medium, conglometrate, sand, chaff charcoal, vermiculite, pearlite or rock wool may be used. In the culture organic medium, bark, natural organic material such as coconut shell, peat moss, sawdust and chaff and organic synthetic products such as polyurethane, polyphenol and vinylon may be used. Among them, the culture in inorganic medium with rock wool is preferable from the viewpoint of an improved retention of nutrient solution and an improved ratio of gas phase.

An applied amount of compound (A) in the nutrient solution culture may be 0.005 kg/10a/culture to 100 kg/10a/culture, more preferably 0.005 kg/10a/culture to 75 kg/10a/culture. It is preferable that a concentration of component (A) of the treating solution and the application number may be adjusted so as to fall within the amount range. The nutrient solution culture is preferable to cultivation of tomato in the invention.

The method of supplying the treating solution may be selected suitably depending on the type of fruit vegetable and the time of application (time of application onto seedlings or the field).

When application of the treating solution onto seedlings and/or the field in the present invention is carried out twice or more, the application is carried out at an interval of preferably 50 days or less, more preferably 10 days or less.

In application onto the field, the treating solution is applied onto a fruit vegetable both under the ground and above the ground. In this case, it is preferable that the treating solution is applied onto the fruit vegetable under the ground at an interval of 50 days or less, and the treating solution is applied to the fruit vegetable above the ground at an interval of 10 days or less.

When the fruit vegetable is a tomato, the treating solution is applied at least once to seedlings in a period of from appearance of leaves to planting, and at least once to the field prior to fruit truss flowering. In this case, the application is conducted preferably plural times during each fruit truss flowering after planting. That is, flowering in the case of tomato starts from the first fruit truss, and the subsequent fruit trusses flower successively, and thus the application is conducted preferably once or plural times in one or more flowering stages of the respective fruit trusses.

The amount of the compound (A) applied is preferably 0.005 kg/10a/culture, 100 kg/10a/culture, preferably 0.005 kg/10a/culture to 75 kg/10a/culture. The concentration of the component (A) and frequency of application are preferably regulated such that the amount of the compound (A) is applied in this range.

The fruit vegetable as the subject of the present invention includes cucumber, pumpkin, watermelon, melon, tomato, eggplant, green pepper, strawberry, okra, string bean, broad bean, pea, soybean (green soybean), corn and the like. Especially, the fruit vegetable as the subject of the invention is preferably tomato, cucumber, strawberry, green pepper and eggplant. Tomato is more preferable.

EXAMPLES

Hereinafter, the present invention is described in more detail by reference to the Examples. The examples are described for merely illustrating the present invention and not intended to limit the present invention.

The treating solutions used in the Examples and Comparative Examples below are shown in Table 1.

TABLE 1

| | Treating solution No. | Compound name | (A)/(B)/(C) ratio by weight |
|---|---|---|---|
| Products of the invention | 1 | (A)Stearyl alcohol<br>(B)POE(20) sorbitane monooleate<br>(C) — | 25/75/0 |
| | 2 | (A)Stearyl alcohol<br>(B)POE(20) sorbitane monooleate<br>(C)EDTA.4Na | 23/69/8 |
| | 3 | (A)1,2-octadecane diol<br>(B)POE(20) sorbitane tristearate<br>(C)3Na citrate | 23/69/8 |
| | 4 | (A)2-octadecanol<br>(B)POE(13) cetyl ether<br>(C) — | 33/67/0 |
| | 5 | (A)Stearyl alcohol<br>(B)Octenyl succinic acid starch<br>(C)3Na citrate | 41/41/18 |
| Comparative product | 6 | (A) —<br>(B)POE(20) sorbitane monooleate<br>(C) — | 0/100/0 |
| | 7 | (A) —<br>(B)POE(20) lauryl ether sodium sulfate<br>(C) — | 0/100/0 |
| | 8 | (A)Decanol<br>(B)POE(20) sorbitan monooleate<br>(C)EDTA.4Na | 23/69/8 |

Examples 1 to 14 and Comparative Examples 1 to 7

A cucumber (Suiseifushinari) was seeded in Kureha compost. After germination and leaf development, treatment was initiated. Using a treating solution prepared by dilution with water such that the component (A) in Table 1 came to be in a predetermined concentration, the plant was treated predetermined times in the stage of seedling with such an amount of water that water overflowed from a pot (for application onto seedlings). A field was prepared in the following manner. The amount of a basal fertilizer applied to the field was designed such that N was 20 kg, $P_2O_5$ was 25 kg and $K_2O$ was 20 kg per 10 ares. Planting was conducted when the number of leaves was 3. At the time of planting, the pot was irrigated with water so as to be wet around the pot. After planting, an additional fertilizer was applied about twice per week depending on the vigor of the plant. The amount of the additional fertilizer applied once was 3 kg/10 ares in terms of nitrogen component. Control of harmful insects was suitably conducted under observation of the state of the plant. In the case of the treatment of the soil (treatment of the plant under the ground), the treating solution containing the component (A) in Table 1 diluted with water at a predetermined concentration was irrigated at predetermined intervals in an amount of 3000 L/10 ares in the usual control of cultivation. In the case of the treatment of leaves and stems (treatment of the plant above the ground), the leaves were treated by spraying with the treating solution in an amount of 500 L/10 ares. The harvest was conducted in accordance with a size standard (height, about 20 cm) in the stage of harvest. The yield was compared as a value relative to that (=100) of a non-treatment section. The results are shown in Table 2.

TABLE 2

| | | Treating solution | | For application | For application onto the field | | | | Yield |
|---|---|---|---|---|---|---|---|---|---|
| | | | | | Treatment of the plant under the ground | | Treatment of the plant above the ground | | |
| | | No. | Concentration of component (A) (ppm) | onto seedlings Number of times | Number of times | Interval (days) | Number of times | Interval (days) | (relative ratio) |
| Example | 1 | 1 | 1 | 2 | 3 | 30 | 12 | 7 | 131 |
| | 2 | 1 | 50 | 2 | 3 | 30 | 12 | 7 | 133 |
| | 3 | 1 | 500 | 2 | 3 | 30 | 12 | 7 | 130 |
| | 4 | 2 | 50 | 3 | 5 | 15 | 20 | 5 | 144 |
| | 5 | 2 | 50 | 2 | 3 | 30 | 12 | 7 | 140 |
| | 6 | 2 | 50 | 2 | 3 | 30 | 9 | 10 | 139 |
| | 7 | 2 | 50 | 1 | 2 | 50 | 12 | 7 | 138 |
| | 8 | 3 | 50 | 2 | 3 | 30 | 12 | 7 | 140 |
| | 9 | 4 | 50 | 2 | 3 | 30 | 12 | 7 | 138 |
| | 10 | 5 | 50 | 1 | 1 | 50 | 1 | 50 | 130 |
| | 11 | 5 | 50 | 1 | 2 | 50 | 12 | 7 | 139 |
| | 12 | 5 | 50 | 2 | 3 | 30 | 9 | 10 | 145 |
| | 13 | 5 | 50 | 2 | 5 | 20 | 12 | 7 | 149 |
| | 14 | 5 | 50 | 3 | 5 | 15 | 20 | 5 | 150 |
| Comparative example | 1 | 1 | 0.5 | 2 | 3 | 30 | 12 | 7 | 106 |
| | 2 | 1 | 50 | 2 | 0 | 30 | 0 | 7 | 104 |
| | 3 | 1 | 50 | 0 | 3 | 30 | 12 | 7 | 111 |
| | 4 | 6 | 0 | 2 | 3 | 30 | 12 | 7 | 101 |
| | 5 | 7 | 0 | 2 | 3 | 30 | 12 | 7 | 97 |
| | 6 | 8 | 50 | 2 | 3 | 30 | 12 | 7 | 80 |
| | 7 | Untreated | — | — | — | — | — | — | 100 |

Examples 15 to 23 and Comparative Examples 8 to 12

A test was conducted on a strawberry (Toyonoka). Seedlings were collected from a parent strain after generation of runners and planted in a seedling field. For raising the seedlings, 4 to 5 grains of a slowly acting fertilizer were used, and an additional liquid fertilizer was applied once per week such that the N component came to be in an amount 3 kg/10 ares. Using a treating solution prepared by dilution with water such that the component (A) in Table 1 came to be in a predetermined concentration, the plant was treated predetermined times in the stage of seedling with such an amount of water that water overflowed from a pot (for application onto seedlings). Thereafter, the plant was planted in the field. The amount of a basal fertilizer applied to the field was designed such that N was 14 kg, $P_2O_5$ was 15 kg and $K_2O$ was 10 kg per 10 ares.

At the time of planting, the plant was irrigated with water so that the soil around the stock was wetted. An additional fertilizer, which was liquid as necessary, was applied about once per week depending on the state of the plant. The liquid fertilizer was applied after dilution to 3 kg/10 ares in terms of nitrogen component. In the customary control of cultivation described above, the treatment in the field was conducted at predetermined intervals by the treating solution containing the component (A) in Table 1 diluted with water at a predetermined concentration. The treatment of the plant under the ground was conducted in an amount of 3000 L/10 ares, and the treatment of the plant above the ground was conducted in an amount of 500 L/10 ares. The harvest was conducted in accordance with a coloration standard in the stage of harvest. The measurement value was compared as a value relative to that (=100) of a non-treatment section. The results are shown in Table 3.

Examples 24 to 32 and Comparative Examples 13 to 18

A green pepper (Kyoyutaka 7) was seeded in Kureha compost. After germination and leaf development, treatment was initiated. Using a treating solution prepared by dilution with water such that the component (A) in Table 1 came to be in a predetermined concentration, the plant was treated predetermined times in the stage of seedling with such an amount of water that water overflowed from a pot (for application onto seedlings). A field was prepared in the following manner. The amount of a basal fertilizer applied to the field was designed such that N was 30 kg, $P_2O_5$ was 45 kg and $K_2O$ was 30 kg per 10 ares. Planting was conducted when the number of leaves was 8, which was just before flowering of a first flower. At the time of planting, the pot was irrigated with water so as to be wet around the pot. After planting, an additional fertilizer was applied about once per week depending on the vigor of the plant so that the plant was not short of the fertilizer. The amount of the additional fertilizer applied once was 3 kg/10 ares in terms of nitrogen component. Control of harmful insects was suitably conducted under observation of the state of the plant. In the case of the treatment of the soil (treatment of the plant under the ground), the treating solution containing the component (A) in Table 1 diluted with water at a predetermined concentration was irrigated at predetermined intervals in an amount of 3000 L/10 ares in the usual control of cultivation. In the case of the treatment of leaves and stems (treatment of the plant above the ground) the leaves were treated by spraying with the treating solution in an amount of 500 L/10 ares. The harvest was conducted in accordance with a size standard in the stage of harvest. The yield was compared as a value relative to that (=100) of a non-treatment section. The results are shown in Table 4.

TABLE 3

| | | Treating solution | | | For application onto the field | | | | |
| --- | --- | --- | --- | --- | --- | --- | --- | --- | --- |
| | | | | | Treatment of the plant under the ground | | Treatment of the plant above the ground | | Yield |
| | No. | Concentration of component (A) (ppm) | For application onto seedlings Number of times | | Number of times | Interval (days) | Number of times | Interval (days) | (relative ratio) |
| Example | 15 | 1 | 50 | 3 | 6 | 30 | 25 | 7 | 139 |
| | 16 | 2 | 50 | 3 | 6 | 30 | 25 | 7 | 145 |
| | 17 | 2 | 50 | 3 | 6 | 30 | 16 | 10 | 141 |
| | 18 | 2 | 50 | 2 | 4 | 50 | 25 | 7 | 140 |
| | 19 | 3 | 50 | 3 | 6 | 30 | 25 | 7 | 142 |
| | 20 | 4 | 50 | 3 | 6 | 30 | 25 | 7 | 140 |
| | 21 | 5 | 50 | 3 | 6 | 30 | 25 | 7 | 145 |
| | 22 | 5 | 50 | 3 | 6 | 30 | 16 | 10 | 141 |
| | 23 | 5 | 50 | 2 | 6 | 50 | 25 | 7 | 143 |
| Comparative example | 8 | 2 | 0.5 | 3 | 6 | 30 | 25 | 7 | 112 |
| | 9 | 6 | 0 | 3 | 6 | 30 | 25 | 7 | 101 |
| | 10 | 7 | 0 | 3 | 6 | 30 | 25 | 7 | 97 |
| | 11 | 8 | 50 | 3 | 6 | 30 | 25 | 7 | 81 |
| | 12 | Untreated | — | — | — | — | — | — | 100 |

TABLE 4

|  | No. | Treating solution | | For application onto seedlings Number of times | For application onto the field | | | | Yield (relative ratio) |
|---|---|---|---|---|---|---|---|---|---|
|  |  |  | Concentration of component (A) (ppm) |  | Treatment of the plant under the ground | | Treatment of the plant above the ground | | |
|  |  |  |  |  | Number of times | Interval (days) | Number of times | Interval (days) |  |
| Example | 24 | 1 | 50 | 2 | 3 | 30 | 12 | 7 | 134 |
|  | 25 | 2 | 50 | 2 | 3 | 30 | 12 | 7 | 141 |
|  | 26 | 2 | 50 | 2 | 3 | 30 | 10 | 10 | 139 |
|  | 27 | 2 | 50 | 1 | 2 | 50 | 12 | 7 | 140 |
|  | 28 | 3 | 50 | 2 | 3 | 30 | 12 | 7 | 143 |
|  | 29 | 4 | 50 | 2 | 3 | 30 | 12 | 7 | 146 |
|  | 30 | 5 | 50 | 2 | 3 | 30 | 12 | 7 | 144 |
|  | 31 | 5 | 50 | 2 | 3 | 30 | 10 | 10 | 140 |
|  | 32 | 5 | 50 | 1 | 2 | 50 | 12 | 7 | 143 |
| Comparative example | 13 | 2 | 50 | 2 | 0 | 30 | 0 | 7 | 112 |
|  | 14 | 2 | 50 | 0 | 2 | 50 | 12 | 7 | 115 |
|  | 15 | 6 | 0 | 2 | 3 | 30 | 12 | 7 | 100 |
|  | 16 | 7 | 0 | 2 | 3 | 30 | 12 | 7 | 99 |
|  | 17 | 8 | 50 | 2 | 3 | 30 | 12 | 7 | 83 |
|  | 18 | Untreated | — | — | — | — | — | — | 100 |

Examples 33 to 41 and Comparative Examples 19 to 23

An eggplant (Chikuyo) was seeded in Kureha compost. After germination and leaf development, treatment was initiated. Using a treating solution prepared by dilution with water such that the component (A) in Table 1 came to be in a predetermined concentration, the plant was treated predetermined times in the stage of seedling with such an amount of water that water overflowed from a pot. A field was prepared in the following manner. The amount of a basal fertilizer applied to the field was designed such that N was 30 kg, $P_2O_5$ was 28 kg and $K_2O$ was 20 kg per 10 ares. Planting was conducted just before flowering of a first flower. At the time of planting, the pot was irrigated with water so as to be wet around the pot. After planting, an additional fertilizer was applied as necessary depending on the vigor of the plant so that the plant was not short of the fertilizer. The amount of the additional fertilizer applied once was 3 kg/10 ares in terms of nitrogen component. Control of harmful insects was suitably conducted under observation of the state of the plant. In the case of the treatment of the soil, the treating solution containing the component (A) in Table 1 diluted with water at a predetermined concentration was irrigated at predetermined intervals in an amount of 3000 L/10 ares in the usual control of cultivation. In the case of the treatment of leaves and stems, the leaves were treated by spraying with the treating solution in an amount of 500 L/10 ares. The harvest was conducted in accordance with a size standard in the stage of harvest. The yield was compared as a value relative to that (=100) of a non-treatment section. The results are shown in Table 5.

TABLE 5

|  | No. | Treating solution | | For application onto seedlings Number of times | For application onto the field | | | | Yield (relative ratio) |
|---|---|---|---|---|---|---|---|---|---|
|  |  |  | Concentration of component (A) (ppm) |  | Treatment of the plant under the ground | | Treatment of the plant above the ground | | |
|  |  |  |  |  | Number of times | Interval (days) | Number of times | Interval (days) |  |
| Example | 33 | 1 | 7 | 2 | 4 | 50 | 15 | 30 | 133 |
|  | 34 | 2 | 7 | 2 | 4 | 50 | 15 | 30 | 141 |
|  | 35 | 2 | 10 | 2 | 4 | 50 | 12 | 30 | 144 |
|  | 36 | 2 | 7 | 1 | 2 | 50 | 15 | 50 | 140 |
|  | 37 | 3 | 7 | 2 | 4 | 50 | 15 | 30 | 137 |
|  | 38 | 4 | 7 | 2 | 4 | 50 | 15 | 30 | 138 |
|  | 39 | 5 | 7 | 2 | 4 | 50 | 15 | 30 | 142 |
|  | 40 | 5 | 10 | 2 | 4 | 50 | 12 | 30 | 145 |
|  | 41 | 5 | 7 | 1 | 2 | 50 | 15 | 50 | 141 |
| Comparative example | 19 | 2 | 7 | 2 | 4 | 0.5 | 15 | 30 | 108 |
|  | 20 | 6 | 7 | 2 | 4 | 0 | 15 | 30 | 99 |
|  | 21 | 7 | 7 | 2 | 4 | 0 | 15 | 30 | 101 |
|  | 22 | 8 | 7 | 2 | 4 | 50 | 15 | 30 | 81 |
|  | 23 | Untreated | — | — | — | — | — | — | 100 |

Examples 42 to 54 and Comparative Examples 24 to 35

A tomato (House Momotaro) was seeded in Kureha compost. After germination and leaf development, treatment was initiated. Using a treating solution prepared by dilution with water such that the component (A) in Table 1 came to be in a predetermined concentration, the plant was treated predetermined times in the stage of seedling with such an amount of water that water overflowed from a pot. A field was prepared in the following manner. The amount of a basal fertilizer applied to the field was designed such that N was 12 kg, $P_2O_5$ was 22 kg and $K_2O$ was 10 kg per 10 ares. Planting was conducted when a first truss had a bud. At the time of planting, the pot was irrigated with water so as to be wet around the pot. After planting, an additional fertilizer was applied about once every 2 weeks depending on the vigor of the plant. The amount of the additional fertilizer applied once was 2 kg/10 ares in terms of nitrogen component. Control of harmful insects was suitably conducted under observation of the state of the plant. In the optimum stage in the usual control cultivation, the plant was treated by irrigating 3000 L/10 ares of the treating solution containing the component (A) in Table 1 diluted with water at a predetermined concentration. Thereafter, the irrigating treatment was conducted successively until the respective fruit trusses flowered. The harvest was conducted in accordance with a color standard in the stage of harvest. The yield was compared as a value relative to that (=100) of a non-treatment section. The results are shown in Table 6. In Table 6, the phrase "Until flowering of first fruit truss" refers to a period of from planting to flowering of a first fruit truss, the phrase "Until flowering of second fruit truss" refers to a period of from flowering of the first fruit truss to flowering of a second fruit truss, and the phrase "Until flowering of third fruit truss" refers to a period of from flowering of the second fruit truss to flowering of a third fruit truss (hereinafter, this definition applies).

Examples 55 to 66 and Comparative Examples 36 to 42

A tomato (House Momotaro) was seeded in Kureha compost. After germination and leaf development, treatment was initiated. Using a treating solution prepared by dilution with water such that the component (A) in Table 1 came to be in a predetermined concentration, the plant was treated predetermined times in the stage of seedling with such an amount of water that water overflowed from a pot. A field was prepared in the following manner. The amount of a basal fertilizer applied to the field was designed such that N was 12 kg, $P_2O_5$ was 22 kg and $K_2O$ was 10 kg per 10 ares. Planting was conducted when a first fruit truss had a bud. At the time of planting, the pot was irrigated with water so as to be wet around the pot. After planting, an additional fertilizer was applied about once every 2 weeks depending on the vigor of the plant. The amount of the additional fertilizer applied once was 2 kg/10 ares in terms of nitrogen component. Control of harmful insects was suitably conducted under observation of the state of the plant. In the optimum stage in the usual control cultivation, the plant was treated by leave-spraying 500 L/10 ares of the treating solution containing the component (A) in Table 1 diluted with water at a predetermined concentration. Thereafter, treatment of leaves was conducted successively until the respective fruit trusses flowered. The harvest was conducted in accordance with a color standard in the stage of harvest. The yield was compared as a value relative to that (=100) of a non-treatment section. The results are shown in Table 7.

TABLE 6

| | | Treating soliution | | Number of times of application | | | | |
| --- | --- | --- | --- | --- | --- | --- | --- | --- |
| | | | | For application onto seedlings at the stage of seedling | For application onto the field | | | |
| | | No. | Concentration of component (A) (ppm) | | At the time of planting | Until flowering of first fruit truss | Until flowering of second fruit truss | Until flowering of third fruit truss | Yield (relative ratio) |
| Example | 42 | 1 | 1 | 3 | 1 | 1 | 1 | 1 | 130 |
| | 43 | 1 | 50 | 3 | 1 | 1 | 1 | 1 | 144 |
| | 44 | 1 | 500 | 3 | 1 | 1 | 1 | 1 | 136 |
| | 45 | 2 | 1 | 3 | 1 | 1 | 1 | 1 | 140 |
| | 46 | 2 | 50 | 3 | 1 | 1 | 1 | 1 | 144 |
| | 47 | 2 | 500 | 3 | 1 | 1 | 1 | 1 | 144 |
| | 48 | 3 | 50 | 3 | 1 | 1 | 1 | 1 | 138 |
| | 49 | 3 | 50 | 3 | 1 | 2 | 2 | 2 | 143 |
| | 50 | 4 | 50 | 3 | 1 | 1 | 1 | 1 | 135 |
| | 51 | 4 | 50 | 1 | 1 | 2 | 2 | 2 | 136 |
| | 52 | 5 | 50 | 1 | 1 | 1 | 1 | 1 | 138 |
| | 53 | 5 | 50 | 3 | 1 | 2 | 2 | 2 | 143 |
| | 54 | 5 | 50 | 5 | 1 | 3 | 3 | 3 | 150 |
| Comparative example | 24 | 1 | 50 | 3 | 0 | 0 | 0 | 0 | 108 |
| | 25 | 1 | 50 | 0 | 1 | 1 | 1 | 1 | 119 |
| | 26 | 2 | 50 | 3 | 0 | 0 | 0 | 0 | 103 |
| | 27 | 2 | 50 | 0 | 1 | 1 | 1 | 1 | 119 |
| | 28 | 3 | 50 | 3 | 0 | 0 | 0 | 0 | 104 |
| | 29 | 3 | 50 | 0 | 1 | 1 | 1 | 1 | 111 |
| | 30 | 4 | 0.5 | 3 | 1 | 1 | 1 | 1 | 110 |
| | 31 | 5 | 0.5 | 3 | 1 | 1 | 1 | 1 | 119 |
| | 32 | 6 | 0 | 3 | 1 | 2 | 2 | 2 | 101 |
| | 33 | 7 | 0 | 3 | 1 | 2 | 2 | 2 | 97 |
| | 34 | 8 | 50 | 3 | 1 | 1 | 1 | 1 | 84 |
| | 35 | Untreated | — | — | — | — | — | — | 100 |

TABLE 7

|  |  | Treating solution | | Number of times of application | | | | | |
|---|---|---|---|---|---|---|---|---|---|
|  |  | | | For application | For application onto the field | | | | |
|  |  | No. | Concentration of component (A) (ppm) | onto seedlings at the stage of seedlings | At the time of planting | Until flowering of first fruit truss | Until flowering of second fruit truss | Until flowering of third fruit truss | Yield (relative ratio) |
| Example | 55 | 2 | 1 | 3 | 1 | 1 | 1 | 1 | 133 |
|  | 56 | 2 | 50 | 3 | 1 | 1 | 1 | 1 | 137 |
|  | 57 | 2 | 500 | 3 | 1 | 1 | 1 | 1 | 131 |
|  | 58 | 2 | 50 | 1 | 1 | 1 | 1 | 1 | 130 |
|  | 59 | 2 | 50 | 3 | 1 | 2 | 2 | 2 | 138 |
|  | 60 | 2 | 50 | 1 | 1 | 2 | 2 | 2 | 136 |
|  | 61 | 5 | 1 | 3 | 1 | 1 | 1 | 1 | 131 |
|  | 62 | 5 | 50 | 3 | 1 | 1 | 1 | 1 | 139 |
|  | 63 | 5 | 500 | 3 | 1 | 1 | 1 | 1 | 134 |
|  | 64 | 5 | 50 | 1 | 1 | 1 | 1 | 1 | 134 |
|  | 65 | 5 | 50 | 3 | 1 | 2 | 2 | 2 | 139 |
|  | 66 | 5 | 50 | 1 | 1 | 2 | 2 | 2 | 134 |
| Comparative example | 36 | 2 | 50 | 3 | 0 | 0 | 0 | 0 | 101 |
|  | 37 | 2 | 50 | 0 | 1 | 1 | 1 | 1 | 114 |
|  | 38 | 5 | 0.5 | 3 | 1 | 1 | 1 | 1 | 113 |
|  | 39 | 6 | 0 | 3 | 1 | 1 | 1 | 1 | 103 |
|  | 40 | 7 | 0 | 3 | 1 | 1 | 1 | 1 | 95 |
|  | 41 | 8 | 50 | 3 | 1 | 1 | 1 | 1 | 79 |
|  | 42 | Untreated | — | — | — | — | — | — | 100 |

Examples 67 to 72 and Comparative Examples 43 to 47

A tomato (House Momotaro) was seeded in Vermiculite. After germination, the tomato was transplanted to a Rock wool pot for seedlings. The pot for seedling was impregnated with a nutrient solution containing Preparation A of House Fertilizer manufactured by Otsuka Chem. Co., Ltd. at a concentration of ½, containing N:P:K=9.3:2.6:4.3 me/l and EC of 1.2 mS/cm. The pot for seedling was impregnated with a liquid diluted with the nutrient solution at ½ concentration of Preparation A of Otsuka Chem. so as to include a given concentration of component (A) of Table 1. The same treatment was conducted until 4.5 leaves of the true leaves.

A field was prepared in the following manner. Rock Wool Slab was used for a cultivating medium. At the time of 4.5 leaves of the true leaves, the tomato was transplanted. The tomato was irrigated in 1 liter per 1 stub with the above shown nutrient solution at concentration of ½ of Preparation A of Otsuka Chem. Control of harmful insects was suitably conducted under observation of the state of the plant. At a suitable stage in usual cultivation, it was irrigated in 1 liter per 1 stub every day with a liquid diluted with the nutrient solution at ½ concentration of Preparation A of Otsuka Chem. so as to include a given concentration of component (A) of Table 1. Thereafter, the irrigating treatment was conducted successively until the respective fruit trusses flowered. The harvest was conducted in accordance with a color standard in the stage of harvest. The yield is shown in comparison with value relative to that (=100) of a non-treatment section. Results are shown in Table 8.

TABLE 8

|  |  | Treating solution | | Number of times of application | | | | | |
|---|---|---|---|---|---|---|---|---|---|
|  |  | | | For application | For application onto the field | | | | |
|  |  | No. | Concentration of component (A) (ppm) | onto seedlings at the stage of seedlings | At the time of planting | Until flowering of first fruit truss | Until flowering of second fruit truss | Until flowering of third fruit truss | Yield (relative ratio) |
| Example | 67 | 2 | 1 | 3 | 1 | 1 | 1 | 1 | 134 |
|  | 68 | 2 | 50 | 3 | 1 | 1 | 1 | 1 | 139 |
|  | 69 | 2 | 500 | 3 | 1 | 1 | 1 | 1 | 139 |
|  | 70 | 5 | 50 | 1 | 1 | 1 | 1 | 1 | 142 |
|  | 71 | 5 | 50 | 3 | 1 | 2 | 2 | 2 | 141 |
|  | 72 | 5 | 50 | 5 | 1 | 3 | 3 | 3 | 144 |
| Comparative examp | 43 | 2 | 50 | 3 | 0 | 0 | 0 | 0 | 105 |
|  | 44 | 2 | 50 | 0 | 1 | 1 | 1 | 1 | 114 |
|  | 45 | 5 | 0.5 | 3 | 1 | 1 | 1 | 1 | 114 |
|  | 46 | 8 | 50 | 3 | 1 | 2 | 2 | 2 | 91 |
|  | 47 | Untreated | — | 0 | 0 | 0 | 0 | 0 | 100 |

The invention claimed is:

1. A method of cultivating a fruit vegetable in an increased yield, which comprises the steps of applying a treating solution comprising a compound (A) at a concentration of 1 to 1000 ppm at least once in a period of from germination of a fruit vegetable to planting in a field, hereinafter, referred to as application onto seedlings, and then applying the solution at least twice after planting in the field, hereinafter, referred to as application onto the field, the compound (A) being represented by the general formula (1):

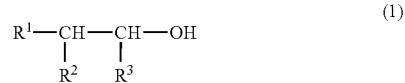

wherein $R^1$ represents a C10 to C22 hydrocarbon group, $R^2$ represents a hydrogen atom, a hydroxyl group or a C1 to C24 hydrocarbon group, and $R^3$ represents a hydrogen atom or a C1 to C24 hydrocarbon group;

wherein said application onto the field is carried out for a fruit vegetable under the ground and above the ground;

wherein the applications of said treating solution onto the fruit vegetable under the ground are carried out at an interval of 30 to 50 days, and the applications of said treating solution onto the fruit vegetable above the ground are carried out at an interval of 10 days or less;

wherein the applications of the above-mentioned treating solution onto seedlings are carried out twice or more at an interval of 50 days or less; and wherein the fruit vegetable is a strawberry, a green pepper, or an eggplant.

2. The method of cultivating a fruit vegetable in an increased yield according to claim 1, wherein the compound (A) is a compound of the general formula (1) wherein $R^2$ and $R^3$ represent a hydrogen atom.

3. The method of cultivating a fruit vegetable in an increased yield according to claim 1, wherein the treating solution further comprises at least one member selected from a surfactant (B) other than the compound (A), a chelating agent (C) and a fertilizer (D).

4. A method of cultivating a fruit vegetable in an increased yield, which comprises the steps of applying a treating solution consisting essentially of a compound (A) at a concentration of 1 to 1000 ppm at least once in a period of from germination of a fruit vegetable to planting in a field, hereinafter, referred to as application onto seedlings, and then applying the solution at least twice after planting in the field, hereinafter, referred to as application onto the field, the compound (A) being represented by the general formula (1):

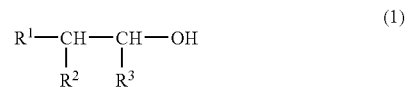

wherein $R^1$ represents a C10 to C22 hydrocarbon group, $R^2$ represents a hydrogen atom, a hydroxyl group or a C1 to C24 hydrocarbon group, and $R^3$ represents a hydrogen atom or a C1 to C24 hydrocarbon group;

wherein said application onto the field is carried out for a fruit vegetable under the ground and above the ground;

wherein the applications of said treating solution onto the fruit vegetable under the ground are carried out at an interval of 30 to 50 days, and the applications of said treating solution onto the fruit vegetable above the ground are carried out at an interval of 10 days or less;

wherein the applications of the above-mentioned treating solution onto seedlings are carried out twice or more at an interval of 50 days or less; and wherein the fruit vegetable is a strawberry, a green pepper, or an eggplant.

5. The method of cultivating a fruit vegetable in an increased yield according to claim 4, wherein the compound (A) is a compound of the general formula (1) wherein $R^2$ and $R^3$ each represent a hydrogen atom.

* * * * *